US011273229B2

(12) United States Patent
Reynolds et al.

(10) Patent No.: US 11,273,229 B2
(45) Date of Patent: Mar. 15, 2022

(54) PHOSPHORIC ACID FREE ANTIMICROBIAL COMPOSITION

(71) Applicant: MIDLAB, INC., Athens, TN (US)

(72) Inventors: Don Euel Reynolds, Lenoir City, TN (US); Matthew Jon Schenk, Athens, TN (US); Courtney Elaine Cosner, Athens, TN (US)

(73) Assignee: Midlab, Inc., Athens, TN (US)

( * ) Notice: Subject to any disclaimer, the term of this patent is extended or adjusted under 35 U.S.C. 154(b) by 111 days.

(21) Appl. No.: 16/744,324

(22) Filed: Jan. 16, 2020

(65) Prior Publication Data

US 2020/0230275 A1 Jul. 23, 2020

Related U.S. Application Data

(60) Provisional application No. 62/793,583, filed on Jan. 17, 2019.

(51) Int. Cl.
*A61L 2/18* (2006.01)

(52) U.S. Cl.
CPC ........... *A61L 2/186* (2013.01); *A61L 2202/20* (2013.01)

(58) Field of Classification Search
CPC ......... A61L 2/186; A01N 25/22; A01N 59/00; C11D 3/00; C11D 3/20; C11D 3/43
See application file for complete search history.

(56) References Cited

U.S. PATENT DOCUMENTS 7,632,523 B2 † 12/2009 Ramirez
8,808,755 B2 † 8/2014 Omidbakhsh
10,450,535 B2 * 10/2019 Ahmadpour .............. C11D 1/83

\* cited by examiner
† cited by third party

*Primary Examiner* — Timothy C Cleveland
(74) *Attorney, Agent, or Firm* — Luedeka Neely Group, PC

(57) ABSTRACT

A disinfectant concentrate devoid of phosphoric acid and method of using the concentrate. The concentration including a mixture containing:
a) a major amount of hydrogen peroxide,
b) a beta hydroxy acid,
c) a minor amount of hydroxyalkane diphosphonic acid, one or more of a solvent and/or surfactant, and the balance water.

17 Claims, No Drawings

PHOSPHORIC ACID FREE ANTIMICROBIAL COMPOSITION

RELATED APPLICATION

This application claims priority to provisional application Ser. No. 62/793,583, filed Jan. 17, 2019.

TECHNICAL FIELD

The disclosure generally relates to antimicrobial and disinfectant compositions which do not leave a contaminating residue upon application to a surface. More specifically, the invention relates to a carboxylic acid/peroxide antimicrobial and disinfectant composition which can provide high antimicrobial efficacy and prevent local environmental bacterial growth and virucidal activity.

BACKGROUND AND SUMMARY

The current state of the art provides a wide variety of antimicrobial and disinfection agents which may be used for any number of purposes. While certain antimicrobial agents such as iodine based agents or quaternary surfactants have a high degree of antimicrobial efficacy, these agents can leave a residue which may be highly undesirable and in fact contaminating of many products or substances which may subsequently come in contact with the treated surface. Accordingly, the treated surface must often be cleansed of the antimicrobial agent by a post-treatment process prior to further use.

For example, hard surface cleaners in food processing environments, dairy compositions such as teat dips, food preparation dips such as those used for cleaning chicken carcasses as well as the human topical cleansers are all compositions which may require an effective antimicrobial agent which does not leave a contaminating residue on the surface of application. Contamination in the context refers to constituent or element resulting from the antimicrobial treatment which is undesirable on the cleaned surface or final product. Such contaminants are largely undesirable in most food processing plants as well as in hospitals and other situations that require sterile environments.

Green initiatives by California and other states, and a number of schools call for safer ways to disinfect and eliminate the use of certain disinfectants such as the reduction or elimination of the use of quaternary ammonium compounds. Peroxide-acid based disinfectant compositions have been selected as providing a suitable alternative to quaternary ammonium containing disinfectants.

However, the present state of the art has not provided a peroxide-acid composition having a durable and high antimicrobial efficacy for use in disinfecting hard surfaces without leaving a residue on the surfaces. There is also a need for a peroxide-acid based composition that is effective antiviral agents.

With regard to the above, the composition of the disclosure provide a disinfectant concentrate, a disinfectant composition and a method for using the composition. The compositions described herein are desirable devoid of phosphoric acid. A suitable concentrate includes a mixture of (a) a major amount of hydrogen peroxide, (b) a beta hydroxy acid, and (c) a minor amount of hydroxyalkane diphosphonic acid. One or more solvents and/or surfactant may be included in the concentrate. The balance of the concentrate is water.

In another embodiment there is provided a virucidal concentrate that includes a mixture of (a) a major amount of hydrogen peroxide, (b) a beta hydroxy acid, and (c) a minor amount of hydroxyalkane diphosphonic acid. One or more solvents and/or surfactant may be included in the concentrate. The balance of the virucidal concentrate is water.

In some embodiments, the beta hydroxy acid of the concentrate is selected from 2-hydroxybenzoic acid, 3-hydroxybutanoic acid, 3-hydroxy-2-phenylpropanoic acid, and 3-hydroxy-3,7,11-trimethyldodecanoic acid. In other embodiments, the beta hydroxy acid is present in the concentrate in an amount ranging from about 0.1 to about 1 wt. % of a total weight of the concentrate.

In some embodiments, the hydrogen peroxide is present in the concentrate in an amount ranging from about 3 to about 5 wt. % of a total weight of the concentrate. In other embodiments, the beta hydroxy acid is present in the concentrate in an amount ranging from about 0.1 to about 1 wt. % of a total weight of the concentrate. In yet other embodiments, the hydroxyalkane diphosphonic acid is present in the concentrate in an amount ranging from about 0.02 to less than about 0.05 wt. % of a total weight of the concentrate. In other embodiments, the solvent is present in the concentrate in an amount ranging from about 5 to about 10 wt. % of a total weight of the concentrate.

In some embodiments, the surfactant in the concentrate is a mixture of anionic and nonionic surfactant. In other embodiments, the nonionic surfactant is present in the concentrate in an amount ranging from about 2 to about 8 wt. % of a total weight of the concentrate. In some embodiments the anionic surfactant is present in the concentrate in an amount ranging from about 4 to about 10 wt. % of a total weight of the concentrate.

In some embodiments, the water is deionized water that is present in the concentrate in an amount ranging from about 50 to about 80 wt. % of a total weight of the concentrate.

In some embodiments, there is provided a disinfectant composition that includes from about 4 to about 10 wt. % of the concentrate and from about 90 to about 96 wt. % water. In other embodiments, there is provided a method for disinfecting surfaces by applying an effective amount of the disinfectant composition to the surfaces. In still other embodiments, the concentrate is a virucidal concentrate and there is provided a method for killing polio viruses on surface by applying an effective amount of a virucidal composition containing the concentrate to the surfaces.

DETAILED DESCRIPTION OF EMBODIMENTS OF THE DISCLOSURE

The compositions described herein generally include a major portion of diluent, solvent or surfactant, and an active antimicrobial agent. The antimicrobial includes a combination of hydrogen peroxide, a beta hydroxy acid, and a minor amount of hydroxyalkane diphosphonic acid.

Hydrogen Peroxide

Among the constituents of the antimicrobial composition, there is present a major amount of hydrogen peroxide. The hydrogen peroxide in combination with the beta hydroxy acid and hydroxyalkane diphosphonic acid provide a surprising and unexpected level of antimicrobial action against organisms including, but not limited to polio viruses.

Hydrogen peroxide, ($H_2O_2$), has a molecular weight of 34.014 and is a weakly acidic, clear, colorless liquid. The four atoms are covalently bound in a nonpolar H—O—O—H structure. Generally, hydrogen peroxide has a melting point of −0.41° C., a boiling point of 150.2° C., a density at 25° C. of 1.4425 grams per cm³ and a viscosity of 1.245 centipoise at 20° C.

While many oxidizing agents may be used, hydrogen peroxide is generally preferred for a number of reasons. First, when combined with the other ingredients listed above at the intended concentrations, hydrogen peroxide contributes to a surprising antimicrobial efficacy many times that of either constituent used separately or other hydrogen peroxide mixtures, including mixtures containing phosphoric acid.

Generally, the concentration of hydrogen peroxide within the concentrate may range from about 3 to about 5 wt. % of the total weight of the concentrate. Disinfectant compositions containing the concentrate may have an effective amount of hydrogen peroxide ranging from about 0.1 to about 0.5 wt. % based on a total weight of the disinfectant composition.

These concentrations of hydrogen peroxide may be increased or decreased while still remaining within the scope of the present disclosure. For example, increasing the concentration of hydrogen peroxide may increase the antimicrobial efficacy of the composition of the present invention. Furthermore increasing the $H_2O_2$ concentration may reduce the need to stabilize the hydrogen peroxide within the composition. Specifically, increasing the hydrogen peroxide concentration in the composition may provide a composition which has an extended shelf life. However, increasing the concentration of hydrogen peroxide past a certain level may be undesirable.

In contrast, decreasing the concentration of hydrogen peroxide may decrease the antimicrobial efficacy of the composition and necessitate the use of an increased concentration of of other antimicrobial components of the composition. Moreover, decreasing the concentration of hydrogen peroxide may necessitate the use of some stabilizing agent to ensure that the composition of the present invention will remain stable over the intended time period.

Beta Hydroxy Acid

Among other constituents, the disinfectant concentrate includes a beta hydroxy carboxylic acid. Carboxylic acids have the general formula R—COOH wherein the R may represent any number of different groups including aliphatic groups, alicyclic groups, aromatic groups, heterocyclic groups, all of which may be saturated or unsaturated as well as substituted or unsubstituted. Hydroxy carboxylic acids also occur having one, two, three or more carboxyl groups and at least one hydroxy group.

Carboxylic acids have a tendency to acidify aqueous compositions in which they are present as the hydrogen atom of the carboxyl group is active and may appear as an ion. The carboxylic acid constituent within the present composition when combined with aqueous hydrogen peroxide generally functions as an antimicrobial agent as a result of the presence of the active hydrogen atom. Moreover, the carboxylic acid constituent within the present composition maintains the composition at an acidic pH.

Carboxylic acids which are generally useful are those having at least one carboxyl groups where the R group is a primary, secondary or tertiary alkyl chain having a length of $C_3$ to $C_{15}$ or an aromatic ring having from $C_1$ to $C_3$ substituents and at least one hydroxy group, preferably a beta hydroxy group ion the ring or substituent. Especially useful are carboxylic acids selected from 2-hydroxybenzoic acid, 3-hydroxybutanoic acid, 3-hydroxy-2-phenylpropanoic acid, 3-hydroxy-3,7,11-trimethyl dodecanoic acid, and the like. Especially preferred is 2-hydroxybenzoic acid, also known as salicylic acid.

The concentration of beta hydroxy acid in the concentrates described herein typically ranges from about 0.1 weight percent to about 1.0 weight percent based on a total weight of the concentrate. A dilute composition containing the concentrate may contain from about 0.006 wt. % to about 0.06 wt. % of the beta hydroxy acid.

Hydroxyalkane Diphosphonic Acid

The addition of a minor amount of phosphorus-based acid in combination with hydrogen peroxide and beta hydroxy acid surprisingly and unexpectedly enhances the bactericidal and/or virucidal activity of aqueous hydrogen peroxide solutions. A minor amount of phosphonic acid or phosphonate in the composition is important to providing stability to the hydrogen peroxide in the composition. However, phosphorus levels must be kept below 0.5 wt. % to meet many state regulations. A phosphonate stability may be replaced with other types of stabilies, e.g., polyacrylic or polyacrylate terpolymers, ethylenediamine tetracidic acid (EDTA), and the like, to achieve peroxide stability. However, many of the other types of stabilizers have problems in that they have limited solubility in the presence of the beta hydroxy acid.

The phosphorus-based acids are inorganic acids or organic acids. Especially preferred are phosphorus-based acids selected from the group consisting of the derivatives of phosphonic acids having 1 to 5 phosphonic acid groups and salts thereof.

More preferably, the phosphorous based acids are phosphonic acids selected from 1-hydroxyethylidene-1,1-diphosphonic acid, diethylenetriaminepenta-(methylene phosphonic acid), 2-hydroxyethylimino bis(methylene phosphonic acid), ethylene diamine tetra(methylene phosphonic acid) and the like.

The preferred phosphorous based acids are known for their sequestering properties and may serve to stabilize the solution against hydrogen peroxide degradation. Stabilizing properties are particularly important in respect of solutions containing higher concentrations of hydrogen peroxide which tend to break down quickly.

Compositions according to the disclosure are desirably devoid of phosphoric acid and have a diphosphonic acid concentration ranging from about of from about 0.02 to less than about 0.05 wt. % of a total weight of the concentrate. A dilute composition containing the concentrate may contain from about 0.001 to less than about 0.003 wt. % of a total weight of the dilute composition.

Surfactants

One or more surfactants may be used in the antimicrobial compositions described herein. In one embodiment, the surfactant includes a mixture of an anionic surfactant and a nonionic surfactant. The anionic surfactant may be selected from carboxylates, sulfonates, and sulfate solubilizing compounds having an alkyl chain ranging from about $C_5$ to about $C_{30}$.

For example, the compositions described herein may include carboxylate surfactants such as polyalkyloxycarboxylates and N-acylsarcosinates; useful sulfonates include alkylaryl sulfonates, alpha olefinsulfonates, and sulfonates with an ester, amide or ether linkages; useful sulfate wetting agents include sulfated alcohols, and sulfated alcohol ethoxylates, sulfated alkylphenols, sulfated acid, amides, and esters, sulfated natural oils and fats as well as agents such as the dioctyl ester of sodium sulfosuccinic acid.

Especially preferable are anionic surfactants such as alkyl or alkyl aromatic sulfonates and sulfates such as alkylbenzene sulfate and sulfonate, and linear alkyl sulfates having a alkyl chain ranging in length from $C_6$ to $C_{20}$. A particularly preferred anionic surfactant is dodecylbenzene sulfonic acid.

Generally, the concentrates described herein may contain from about 4 to about 10 wt. % of the anionic surfactant based on a total weight of the concentrate. A dilute solution containing the concentrate may contain from about 0.2 to about 0.6 wt. % of the anionic surfactant based on a total weight of the dilute composition.

The nonionic surfactant may include one or more alkylated alkoxylate surfactants, such as polyoxyethylene surfactants. Suitable polyoxyethylene surfactants may be selected from alkyl polyoxyethylene surfactants and alkyl aryl polyoxyethylene surfactants. A preferred alkyl polyoxyethylene surfactant is a linear primary alcohol ethoxylate such as a $C_6$-$C_{10}$ alkyl compound containing 3.5 moles of ethylene oxide (EO). Also, preferred alkyl aryl polyoxyethylene surfactants that are $C_8$ to $C_{16}$ alkylphenol alkoxylates.

Generally, the concentrates described herein may contain from about 2 to about 8 wt. % of the nonionic surfactant based on a total weight of the concentrate. A dilute solution containing the concentrate may contain from about 0.1 to about 0.5 wt. % of the nonionic surfactant based on a total weight of the dilute composition.

Solvent

Preferred as solvents for use in the compositions described herein are glycol ethers having the general structure Ra—O—Rb—OH, wherein Ra is an alkoxy of 1 to 20 carbon atoms, or aryloxy of at least 6 carbon atoms, and Rb is an ether condensate of propylene glycol and/or ethylene glycol having from 1 to 10 glycol monomer units. Examples of preferred glycol ethers include ethylene glycol monobutyl ether, diethylene glycol monobutyl ether as well as butoxypropanol, propoxypropanol, mono-, di- and tri-propylene glycol butyl ethers, and mixtures thereof.

Desirably, the glycol ether solvent is preferably present in the concentrate in an amount ranging from about 5 to about 10 wt. % based on a total weight of the concentrate. A dilute solution of the concentrate may contain from about 0.3 to about 0.6 wt. % of the glycol ether based on a total weight of the dilute composition. The glycol ether solvent present in the compositions described herein have been found to provide enhanced cleaning and to assist in solubilizing the beta hydroxy acid, but are not present in excessive amounts which may reduce the overall stability of the cleaning and disinfecting compositions being taught herein.

The antimicrobial composition of the present disclosure may also comprise any number of adjuvants. Specifically, the composition of the present invention may comprise stabilizing agents, wetting agents, skin conditioning agents as well as pigments or dyes among any number of constituents which may be added to the composition.

Stabilizing agents may be added to the composition of the present invention to stabilize the hydrogen peroxide and prevent the premature oxidation of this constituent within the composition of the present invention.

A dye may also be used as an adjuvant within the compositions of the present disclosed embodiments. Due to the diluted nature of these compositions, they may often be confused with a bucket of water and ingested. In order to avoid such an occurrence the antimicrobial composition of the present invention may be dyed so that it may clearly be identified.

The dye or pigment used in the composition described herein may be any organic or inorganic dye which is a chemically acceptable trace constituent on the surfaces to which it is to be applied. Generally, dyes which are useful in the composition of the present invention include F, D & C Yellow Nos. 5 and 6. Although any number of colorants may be used, these dyes are preferred due to their relative acceptability in various solid and liquid food systems.

Generally, the dyes or pigments used within the present invention may be present in a concentration ranging from about 0.001 wt-% to 0.01 wt-%, preferably from about 0.002 wt-% to 0.006 wt-%, and most preferably from about 0.002 wt-% to 0.004 wt-% based on a total weight of the dilute compositions.

The present composition may also contain any other number of constituents such as fragrances, among other constituents which are well known to those skilled in the art and which may facilitate the activity of the present invention.

The following non-limiting examples are given to further illustrate the advantages of the present disclosed embodiments. In the examples, the following concentrate was used.

| Disinfectant Concentrate | |
|---|---|
| Raw Material | Wt. % |
| DI Water | 67.30 |
| phosphonic acid 60% active | 0.058 |
| Phosphoric Acid 75% | 0.00 |
| Anionic surfactant | 7.00 |
| Nonionic surfactant | 5.00 |
| 35 wt. % hydrogen peroxide in water | 12.14 |
| Glycol ether solvent | 8.00 |
| Beta hydroxy acid | 0.50 |

Test Parameters
Dilution: 8 oz in one gallon of water–1 part test substance+ 16.84 parts 200 ppm AOAC Synthetic Hard Water
Virus: Poliovirus type 1, ATCC VR-1562, Strain Chat
Exposure time: 5 minutes
Exposure Temperature: Room temperature (21.0° C.)

Organic soil load: 5% fetal bovine serum

Test Medium: Minimum Essential Medium (MEM) supplemented with 5% (vlv) heat-inactivated fetal bovine serum, 100 units/mL penicillin, 10 pg/mL gentamicin, and 2.5 pg/mL amphotericin B.

Indicator Cell Cultures: Vero cells

Experimental

A film of virus dried on a glass surface was exposed to a 2.00 mL aliquot of the use dilution of the test substance for the 5 minute specified exposure time at room temperature (21.0° C.). Following the exposure time, the virucidal and cytotoxic activities were removed from the virus-test substance mixtures utilizing a Sephadex gel column, and the mixture was assayed for viral infectivity by an accepted assay method. Appropriate virus, test substance cytotoxicity, and neutralization controls were run concurrently. The study was not conducted under US EPA 40 CFR Part 160 or US FDA 21 CFR Part 58.

Conclusion

Under the conditions of this investigation and in the presence of a 5% fetal bovine serum organic soil load, the disinfectant concentrate was diluted 8 oz in one gallon of water defined as 1 part test substance+16.84 parts 200 ppm AOAC Synthetic Hard Water. The dilute solution demonstrated complete inactivation of Poliovirus type I following a 5 minute exposure time at room temperature (21.0° C.).

Taking the cytotoxicity and neutralization control results into consideration, a ≥4.00 $\log_{10}$ reduction in viral titer was demonstrated.

TABLE 1

Virus Controls and Test Results
Effects of HP2O2 [Sample D (Batch# 0917181)]
Following a 5 Minute Exposure to Poliovirus
Type 1 Dried on an Inanimate Surface

| Dilution | Input Virus Control | Dried Virus Control | Poliovirus type 1 + Sample D (Batch# 0917181) |
|---|---|---|---|
| Cell Control | 0 0 | 0 0 0 0 | 0 0 0 0 |
| $10^{-1}$ | + + | + + + + | 0 0 0 0 |
| $10^{-2}$ | + + | + + + + | 0 0 0 0 |
| $10^{-3}$ | + + | + + + + | 0 0 0 0 |
| $10^{-4}$ | + + | + + + + | 0 0 0 0 |
| $10^{-5}$ | + + | + + + + | 0 0 0 0 |
| $10^{-6}$ | + + | 0 0 0 0 | 0 0 0 0 |
| $10^{-7}$ | + + | NT | NT |
| $10^{-8}$ | 0 0 | NT | NT |
| $TCID_{50}$/100 μL | $10^{7.50}$ | $10^{5.50}$ | $\leq 10^{0.50}$ |

+ = Positive for the presence of test virus
0 = No test virus recovered and/or no cytotoxicity present
NT = Not tested

TABLE 2

Cytotoxicity and Neutralization Control Results

| Dilution | Cytotoxicity Control Sample D (Batch# 0917181) | Neutralization Control Test Virus + Cytotoxicity Control Sample D (Batch# 0917181) |
|---|---|---|
| Cell Control | 0 0 0 0 | 0 0 0 0 |
| $10^{-1}$ | T T T T | T T T T |
| $10^{-2}$ | 0 0 0 0 | + + + + |
| $10^{-3}$ | 0 0 0 0 | + + + + |
| $10^{-4}$ | 0 0 0 0 | + + + + |
| $10^{-5}$ | 0 0 0 0 | + + + + |
| $10^{-6}$ | 0 0 0 0 | + + + + |
| $TCID_{50}$/100 μL | $10^{1.50}$ | Neutralized at a $TCID_{50}$/100 μL of ≤1.50 $\text{Log}_{10}$ |

0 = No test virus recovered and/or no cytotoxicity present
T = Cytotoxicity present The composition of the disclosed embodiments may be applied on the intended surfaces without the formation of any antimicrobial contaminating residue upon such surfaces. Application of the compositions described herein provide a high antimicrobial efficacy which once applied leaves a residue which is noncontaminating.

The composition described herein may be used in many environments where the provision of a noncontaminating high efficacy antimicrobial composition is desired.

The composition described herein may also be used in any variety of other environments where a postprocessing wash or drying is not preferable or desired. For instance, the composition of the present invention may be used as a topical hand wash. Alternatively, the compositions may be used in food preparation environments on hard porous or nonporous surfaces. For instance, certain surfaces within food preparation environments are porous and in fact will absorb any active antimicrobial. Consequently, a post disinfecting washing or drying may not always be effective in removing the antimicrobial from the food preparation surface.

In contrast, by using the compositions of the present disclosure to clean the food preparation surfaces post treatment drying or washing is unnecessary. The disclosed compositions also the potential for recontaminating the surface of application by such post-treatment processing.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications, variations, improvements, and substantial equivalents.

What is claimed is:

1. A disinfectant concentrate devoid of phosphoric acid, consisting essentially of:
    a mixture of:
        a) from about 3 to about 5 wt. % of hydrogen peroxide based on a total weight of the concentrate,
        b) a beta hydroxy acid in an amount ranging from about 0.1 to less than 1 wt. % based on a total weight of the concentrate,
        c) from about 0.02 to less than 0.05 wt. % of hydroxyalkane diphosphonic acid based on a total weight of the concentrate,
    one or more glycol ether solvents in an amount ranging from about 5 to about 10 wt. % based on a total weight of the concentrate,
    optionally, one or more surfactants in an amount ranging from about 2 to about 10 wt. % based on a total weight of the concentrate, and
    the balance water, wherein the disinfectant concentrate is devoid of non-surfactant sulfonic acid(s).

2. The disinfectant concentrate of claim 1, wherein the beta hydroxy acid is selected from the group consisting of 2-hydroxybenzoic acid, 3-hydroxybutanoic acid, 3-hydroxy-2-phenylpropanoic acid, and 3-hydroxy-3,7,11-trimethyl dodecanoic acid.

3. The disinfectant concentrate of claim 1, wherein the surfactants comprise a mixture of anionic and nonionic surfactants.

4. The disinfectant concentrate of claim 3, wherein the nonionic surfactants are present in an amount ranging from about 2 to about 8 wt. % of a total weight of the concentrate.

5. The disinfectant concentrate of claim 3, wherein the anionic surfactants are present in an amount ranging from about 4 to about 10 wt. % based on a total weight of the concentrate.

6. The disinfectant concentrate of claim 1, wherein the water comprises deionized water in an amount ranging from about 50 to about 80 wt. % of a total weight of the concentrate.

7. A disinfectant composition comprising from about 4 to about 10 wt. % of the disinfectant concentrate of claim 1 and from about 90 to about 96 wt. % water, wherein the disinfectant composition is devoid of non-surfactant sulfonic acid(s).

8. A method for disinfecting surfaces comprising applying an effective amount of the disinfectant composition of claim 7 to the surfaces.

9. A virucidal concentrate consisting essentially of:
a virucidal mixture of:
- a) from about 3 to about 5 wt. % of hydrogen peroxide based on a total weight of the concentrate,
- b) a beta hydroxy acid in an amount ranging from about 0.1 to less than 1 wt. % based on a total weight of the concentrate,
- c) from about 0.02 to less than 0.05 wt. % of hydroxyalkane diphosphonic acid based on a total weight of the concentrate, one or more of glycol ether solvents in an amount ranging from about 5 to about 10 wt. % based on a total weight of the concentrate, optionally, one or more surfactants in an amount ranging from about 2 to about 10 wt. % based on a total weight of the concentrate, and the balance water, wherein the virucidal concentrate is devoid of non-surfactant sulfonic acid(s).

10. The virucidal concentrate of claim 9, wherein the concentrate is devoid of phosphoric acid.

11. The virucidal concentrate of claim 9, wherein the beta hydroxy acid is selected from the group consisting of 2-hydroxybenzoic acid, 3-hydroxybutanoic acid, 3-hydroxy-2-phenylpropanoic acid, and 3-hydroxy-3,7,11-trimethyl dodecanoic acid.

12. The virucidal concentrate of claim 9, wherein the surfactants comprise a mixture of anionic and nonionic surfactants.

13. The virucidal concentrate of claim 12, wherein the nonionic surfactants are present in an amount ranging from about 2 to about 8 wt. % of a total weight of the concentrate.

14. The virucidal concentrate of claim 12, wherein the anionic surfactants are present in an amount ranging from about 4 to about 10 wt. % based on a total weight of the concentrate.

15. The virucidal concentrate of claim 9, wherein the water comprises deionized water in an amount ranging from about 50 to about 80 wt. % of a total weight of the concentrate.

16. A virucidal composition comprising from about 4 to about 10 wt. % of the virucidal concentrate of claim 9 and from about 90 to about 96 wt. % water wherein the virucidal composition is devoid of non-surfactant sulfonic acid(s).

17. A method for killing polio viruses on surfaces comprising applying an effective amount of the virucidal composition of claim 16 to the surfaces.

* * * * *